United States Patent [19]

Tabacco et al.

[11] Patent Number: 5,268,972
[45] Date of Patent: Dec. 7, 1993

[54] AROMATIC HYDROCARBON OPTRODES FOR GROUNDWATER MONITORING APPLICATIONS

[75] Inventors: Mary E. Tabacco, Brighton, Mass.; Bruce J. Nielsen, Panama City, Fla.

[73] Assignee: The United States of America as represented by the Secretary of the Air Force, Washington, D.C.

[21] Appl. No.: 834,091

[22] Filed: Feb. 12, 1992

[51] Int. Cl.$^5$ .............................................. G02B 6/02
[52] U.S. Cl. ........................................ 385/2; 385/13; 385/123; 65/3.15
[58] Field of Search ................ 385/12, 13, 123, 43; 65/3.15, 3.20, 3.30

[56] References Cited

U.S. PATENT DOCUMENTS 4,846,548  7/1979  Klainer .................................. 385/12
5,109,442  4/1992  Klainer et al. ................... 385/123 X

OTHER PUBLICATIONS

Shahriari et al. "Porous Fiber Optic for Chemical Sensors" 1st International Symposium'Field Screening Methods for Hazardous Waste Site Investigations, 1988.
Shahriari et al. "Porous optical fibers for high-sensitivity ammonia-vapor sensor" Optics Letters, vol. 13, No. 5, May 1988.
Giuliani et al., "Reversible Optical Waveguide Sensor for Ammonia Vapors" Optics Letters, vol. 8, No. 11, Jan. 1983.
Ballantine "Optical Waveguide Humidity Detector" Analytical Chemistry, vol. 58, No. 3, Nov. 1986.

*Primary Examiner*—John D. Lee
*Assistant Examiner*—Phan Heartney
*Attorney, Agent, or Firm*—Mervin L. Jordan; Donald J. Singer

[57] ABSTRACT

Fiber optic based optrodes suitable for in-situ monitoring of groundwater and earth material for the presence of aromatic hydrocarbons. The optrodes are fabricated with porous optical waveguides which are impregnated with a chemical indicator whose optical transmission properties change in the presence of aromatic species, providing a high degree of chemical specificity.

6 Claims, 6 Drawing Sheets

AROMATIC HYDROCARBON OPTRODES FOR GROUNDWATER MONITORING APPLICATIONS

FIELD OF THE INVENTION

The invention relates to fiber optic based optrodes (sensors) suitable for in-situ monitoring of groundwater and earth material for the presence of aromatic hydrocarbons. In particular, the invention relates to fiber optic based optrodes using porous waveguides sensitive to the presence of aromatic hydrocarbons and to a method of fabricating same.

BACKGROUND OF THE INVENTION

The use of optical fibers as components of chemical sensors for in-situ monitoring of different chemical species is a recent development. For example, various researchers have successfully demonstrated the use of porous fiber sensors for the measurement of humidity, pH, ammonia, and carbon monoxide. In this regard, attention is directed to the works of Shahriari et al referenced in the First International Symposium on Field Screening Methods for Hazardous Waste Site Investigations, Las Vegas, Nev. (1988), Proceedings of the International Society for Optical Engineering, Vol. 838 Fiber Optic and Laser Sensors V, page 348, (August 1987), Optics Letters, Vol, 13, page 407 (May 1988), and Zhou et al (International Journal of Optoelectronics, 1989, Vol. 4, page 415).

The general approach taken with respect to these sensors involves the interaction of light which propagates through the fiber interacting with a reagent that, in turn, selectively interacts with the environment to be sensed. The typical optical properties monitored include evanescant absorption and fluorescence, and chemiluminescence. The reagents are normally immobilized into a membrane or porous polymer matrix and then coated either on the tip or side of the fiber.

One of the problems encountered with fiber optic chemical sensors based on evanescent absorption has been identified by researchers as low sensitivity attributable to the limited depth of penetration of evanescent light into the reagent cladding. These researchers include Giuliani et al (Optical Letters, Vol, 8, page 54, 1983), Russell et al (Anal. Chem. Actal., Vol. 170, page 209, 1985), Ballantine et al (Analytical Chemistry Vol 58 page 2883, 1986), and Zhu et al (Journal of Electrochemical Society, 1987, Vol. 136 (2); page 567).

As part of the effort to overcome this prior art problem, a high sensitivity chemical sensor employing porous glass fibers was designed and developed. The theory underlying this effort was that in a typical evanescent fiber optic sensor, the sensitivity is limited both by the depth of penetration of evanescent light into the reagent coated on the fiber core, and the number of internal reflections, whereas in a porous fiber, the analyte, i.e., the chemical species to be sensed, would penetrate into the pores and interact with the reagent which would have been cast previously into the pores. Since the porous fiber would have a large surface area, it is theorized that the absorption would be enhanced dramatically, leading to an optrode with high sensitivity. Another advantage theorized with a porous glass fiber would be the small sensing region (about 0.5 cm in length and 250 microns in diameter) which would be an integral part of the fiber waveguide. Theoretically, this latter feature would be expected to eliminate the complications associated with the physical and optical coupling of the sensor probe to the fiber. In addition, multiple fiber sensors would be deployed from a single analytical unit and would be expected to be less expensive than conventional sensors based on materials cost and ease of fabrication.

SUMMARY OF THE INVENTION

The invention relates to fiber optic based optrodes suitable for in-situ monitoring of groundwater and earth material for the presence of aromatic hydrocarbons. The inventive feature resides in the fabrication of the optrodes with borosilicate optical fibers which are provided with porous waveguides by heat treating and acid leaching. The porous waveguides offer the advantages of greatly increased interactive surface area, which dramatically improves sensitivity, and a continuous optical path, thereby eliminating mechanical and coupling losses. The porous section of fiber is impregnated with a chemical indicator whose optical transmission properties change in the presence of aromatic species, providing a high degree of chemical specificity. The inventive optrodes are characterized by sensitivity to <50 ppb, response time <1 minutes, excellent reporoducibility and linearity, and specificity for aromatic fuel constituents.

OBJECTS OF THE INVENTION

Accordingly, a principal object of the invention is to provide a fiber optic based optrode suitable for in-situ monitoring of groundwater and earth material for the presence of aromatic hydrocarbons.

Another object of the invention is to provide a fiber optic based optrode having porous waveguides sensitive to the presence of aromatic hydrocarbons.

A further object of the invention is to provide a fiber optic based optrode fabricated with borosilicate optical fibers which are provided with porous waveguides by heat treating and acid leaching.

Yet another object of the invention is to provide a method of fabricating a fiber optic based optrode for in-situ monitoring of groundwater and earth material for aromatic hydrocarbons.

Other objects and advantages of the invention will be apparent to those skilled in the art upon reference to the accompanying drawings and detailed description.

DETAILED DESCRIPTION OF THE INVENTION

Figure 1A:
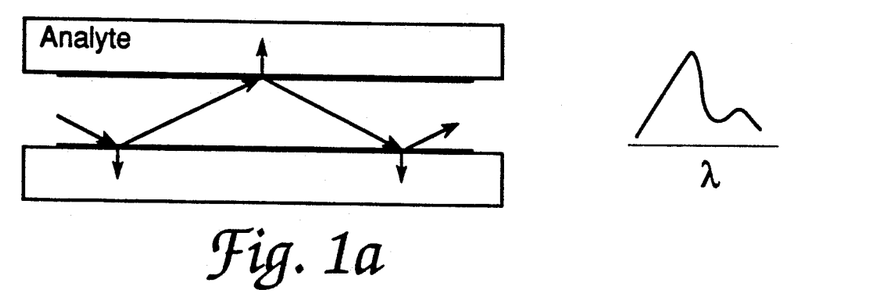
FIGS. 1a, 1b and 1c are schematic diagrams comparing basic sensor designs.
Figure 1B:
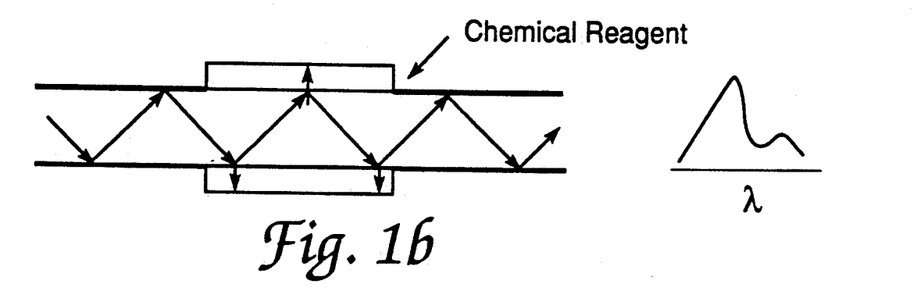
Figure 1C:
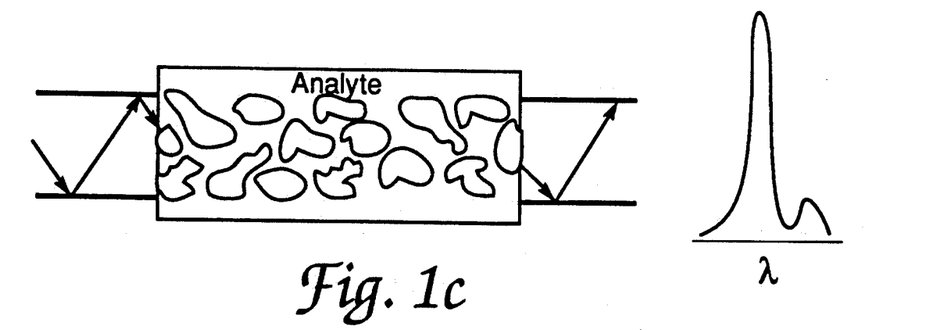
Figure 2:
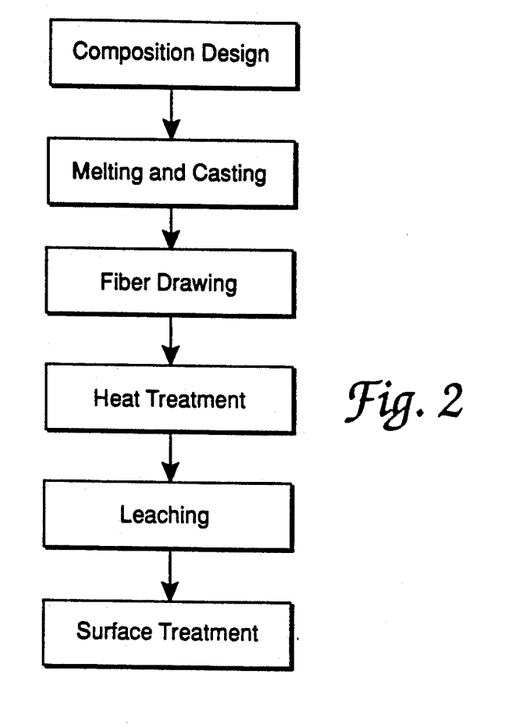
FIG. 2 is a flow diagram of the processing steps for producing porous glass fibers.

The porous optical fibers used in the fabrication of the inventive optrodes employ a material comprising an alkali borosilicate glass with the composition $SiO_2$, $B_2O_3$ and alkali oxides. This type of glass is a well characterized system, producible at a low cost and most importantly it exhibits the phenomenon of liquid/liquid immiscibility within a certain temperature range. The above composition is melted in an electrical furnace at 1400° C. and cast into rods with a 20 mm diameter and 0.5 m in length. The rods are drawn into fibers at about 700° C. by a draw tower equipped with an electrical furnace. Fibers with a 250–300 micron diameter and several meters long are produced this way. A portion of fiber (about 5–10 cm in length) is then heat treated in a tube furnace at 600° C. for about 3 hours. At this point the heat treated glass is phase separated, one phase silica rich and the other boron rich. The boron rich phase is leached out of the glass by placing the fiber in a bath of hydrochloric acid. The fibers are subsequently washed with distilled water and rinsed with alcohol. FIG. 2 illustrates the processing steps for fabricating porous fibers.

Subsequent to the fiber preparation, a porous segment (typically <1 cm) is cast with the sensing reagent (indicator). This is done by dissolving the reagent in a solvent at a predetermined concentration and soaking the porous fiber in the solution. The reagent is then dried into the pores by air drying or heating the fiber in a low temperature oven.

The simple aromatic components of fuel, such as benzene, toluene, ethylbenzene and xylene (BTEX) are quite stable by virtue of resonance electron effects, and the modest electron donating or withdrawing capability of the methyl (—$CH_3$) substituents. A number of indicator solutions were tested for room temperature response to the simple aromatics (in both the vapor and liquid state).

The indicators tested included tetracyanoquinodimethane (TCNQ), fluorescein, $AgNO_3$, (and $AgNO_3$ "mirror" solution), maleic anhydride, $I_2$ and tetracyanoethylene (TCNE). There is evidence (Merrifield et al, J. Am. Chem. Soc., Vol. 80, page 2778, 1958) that the aromatics will form $\pi$-type complexes, or adducts with the latter three species. In this case the aromatic is considered a $\pi$-base, and the maleic anhydride, $I_2$ or TCNE is the $\pi$-acid. Only the $I_2$ and the TCNE formed complexes which exhibited a visible color change upon complexation. The iodine-benzene adduct produces a color change in the visible, but is limited practically by the volatility, and ready sublimation, of the $I_2$ reagent.

TCNE [$(CN)_2 C=C(CN)_2$] forms colored complexes with benzene, toluene and xylene which progress from yellow to reddish-orange, respectively. The complexes are believed to be 1:1 adducts in which the species lie parallel to one another. This would ensure maximum overlap of the $\pi$-molecular orbitals of the components. In solution, the adducts exhibit broadband absorption with peaks from 384 nm to 460 nm.

O-xylene was chosen as the target aromatic species for sensor characterization and evaluation because of its strong complex formation with TCNE, Reference 9, and an adduct absorption peak which overlaps well with the inherent transmission properties of the optical fiber (optical transmission in silica fiber falls off in the near UV).

The TCNE concentrations used in our experiments varied from 0.5 mg/ml to 10 mg/ml in dichloromethane. In the early experiments acetone was used as the solvent; this solution had a faint yellow color and turned black upon standing a few days. This may be explained by the formation of a competitive TCNE/solvent complex, See Middleton et. al. J. Am. Chem. Soc. 80, 2783 (1958).

No such stability problems were encountered when using dichloromethane as the solvent. Indicator solutions could be used for at least a week with no compromise in data reproducibility.

Figure 3:
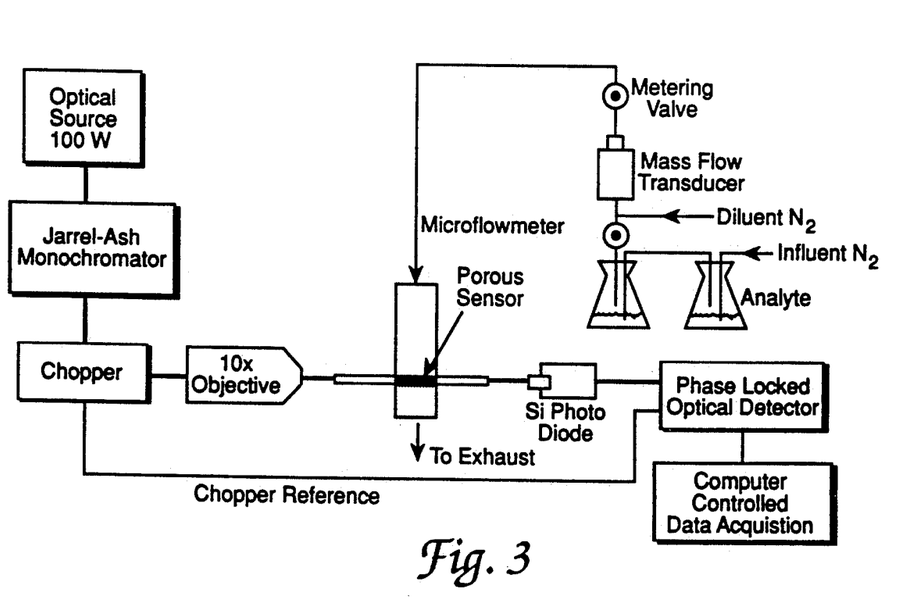
FIG. 3 is a schematic diagram of an optical system and test be for optrode evaluation.

A schematic of the optical system and test bed is shown in FIG. 3. The porous sensor is housed in a glass or brass tube, with holes drilled to admit the fiber. The fiber is held in place with an optically inactive adhesive. Sections of porous fiber, ~2.5 cm in length, were cleaved from the longer sections provided by Rutgers. These were examined under a microscope to check the optical injection surfaces. Shorter regions (~0.5–1 cm in length) were then made into sensing regions by treatment with the indicator.

The light source is a 100 W tungsten-halogen lamp (typically operated at 70 W), which is focused into an externally controlled Jarrell-Ash monochromator for wavelength selection and rapid scanning of the relevant spectra. The monochromatic light is chopped at a reference frequency (2005 Hz), focused with a microscope objective and launched into the sensing fiber. The transmitted light is detected by a silicon photodiode, coupled to a lock-in amplifier and computer controlled data acquisition system.

Most of the light launched into the fiber interacts with the indicator or other chemical reagents introduced into the waveguide. "In-line" optical absorption occurs and is very strong, as in the case of a long pathlength absorption cell. Light loss due to scattering by the porous glass host is approximately 0.7 dB/cm which, does not compromise sensitivity over such short lengths.

Referring to FIG. 3, a nitrogen ($N_2$) stream saturated with xylene vapor is obtained by bubbling the inert gas through a multiple stage sparging apparatus. The liquid level of the last stage of the sparge line is monitored for fluid level change. No change ensures a saturated vapor stream. The xylene flow is regulated by either a Gilmont microflowmeter (sub ppm) or Matheson digital mass flow transducer (low ppm) depending on the flow range of interest, and is diluted with additional $N_2$. All gas flow lines are stainless steel, and after passage through the sensing region the vapor is exhausted to a fume hood. A sample xylene concentration calculation is presented in Appendix A.

A typical experimental run to determine optrode sensitivity and response time involves the following steps:

1. Scan intensity versus wavelength (350–550 nm) of untreated porous fiber to check inherent transmission.
2. Impregnate section (~0.5–1 cm) of fiber with indicator of known concentration. This is now the sensor, or optrode.
3. Start diluent $N_2$ flow ($\leq 600$ cm).
4. Realign to optimize transmission, and record intensity versus wavelength from 350–550, and 600–800 nm (reference wavelength is ~700 nm).
5. Reposition monochromator to desired interrogation wavelength.
6. Open xylene/$N_2$ sparge line and adjust with fine metering valve to desired flowrate.
7. Record intensity versus time until saturation is reached.
8. Rescan 350–500 nm, and 600–800 nm (to check reference wavelength).

There are two primary functions of the data acquisition system: control of the monochromator grating angle (which allows light of known wavelengths and bandwidth to be selected), and detection of the light intensity at that wavelength. An analysis of the initial setup revealed several factors which would affect evaluation of the sensor performance. The quality of the interrogating source is determined by the precision of the wavelength step interval, and accuracy of the wavelength chosen by the grating mechanism. These factors affect evaluation of the sensor spectroscopic characteristics. Detection of the sensor output is limited by the recording rate of the output device.

The accuracy of the interrogating light source, and hence resolution, was not acceptable because of the mechanical limits of the original monochromator grating mechanism. A stepper motor interface provided the finite steps of high accuracy and resolution, as well as repeatability. To access the power of the stepper motor system, a computer controller was incorporated. The Computer Continuum lab 40-5 stepper motor system provided IBM-PC compatibility with simplicity of operation and low cost.

An analysis of the detection components of the sensor system revealed that reading of the analog output of the lock-in amplifier (used to detect the sensor response) would either limit resolution, or compromise the rate of data acquisition. In the case of a rapidly responding sensor operating in real time, the condition was unacceptable. A GPIB data acquisition system with a digital voltmeter (DVM) was incorporated to digitize the analog output of the lock-in, which increased the acquisition rate, thereby, increasing the resolution to 1 part in 65,500.

With these components under computer control, the two systems were functionally integrated. Software was developed to acquire an intensity value at a particular wavelength. The motor then steps a quantified amount to the next wavelength of interest, acquiring another data point until the final wavelength of interest was reached. The result, a plot of light intensity as a function of scanned wavelength, was displayed on the computer as mV versus wavelength. A program was also developed which took the ratio of the spectroscopic curves before and after exposure to the chemical of interest, thereby, revealing details of the absorption feature.

The scanning wavelength program was used to return to the specified interrogation wavelength and the system was poised to measure variations in the intensity with respect to time. A data acquisition rate could be set depending on the sensor response time. The output shows intensity of light in mV versus time. The information contained in this scan shows sample response time and saturation level. The slope of this graph is linearly related to analyte concentration as discussed in Appendix B.

Figure 4:
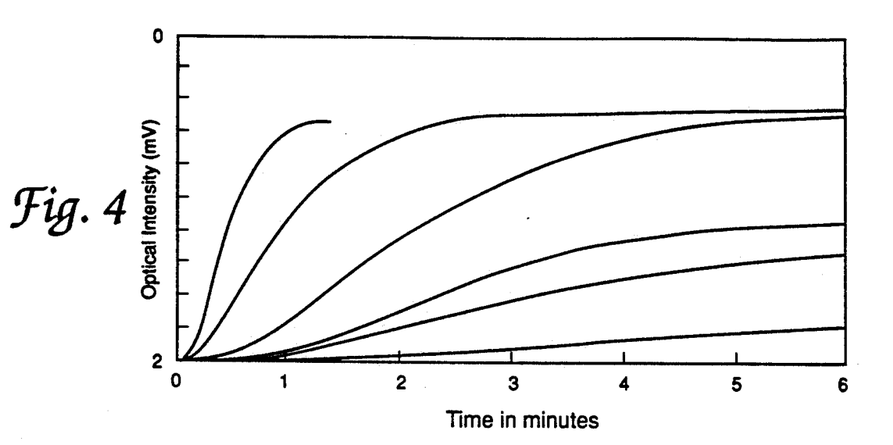
FIG. 4 is a plot of response curves for a porous glass xylene sensor at 470 nm and 0.5 mg/ml TCNE for xylene concentrations ranging from 2 ppm to $f$ 40 ppb.
Figure 5:
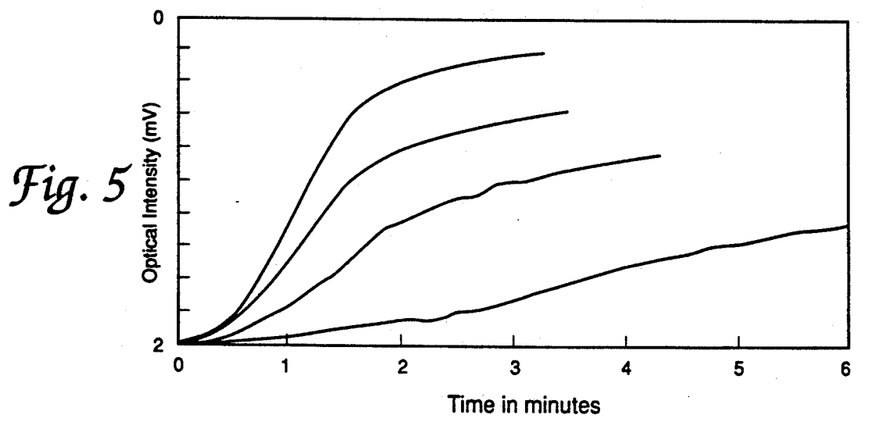
FIG. 5 is a plot of response curves for a porous glass xylene sensor at 470 nm and 0.5 mb/ml TCNE for xylene concentrations ranging from 320 ppb to <40 ppb.
Figure 6:
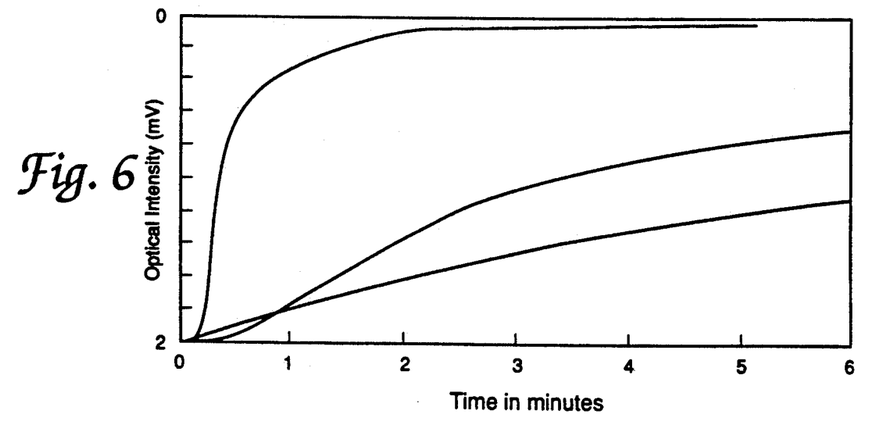
FIG. 6 is a plot of response curves for a porous glass xylene sensor at 470 nm and 10 mg/ml TCNE for xylene concentrations ranging from 1 ppm to $f$ 40 ppb.

Optrodes were fabricated and evaluated for sensitivity, response time, reproducibility, and linearity with xylene as the target species. The interrogation wavelength for intensity versus time plots was 470 nm, which is near the peak absorption for the TCNE:xylene adduct formed. There is increased absorption in the blue (which corresponds to decreasing transmission intensity) as the xylene reacts with the TCNE. Summaries of the intensity versus time curves are presented in FIGS. 4–6. These data are representative of a minimum of two (and often more) experimental runs. The excellent sensitivity of the optrodes (~40 ppb) with near real time response (<1 minute) is note worthy. The actual intensity changes are 2–3 orders of magnitude.

Figure 7:
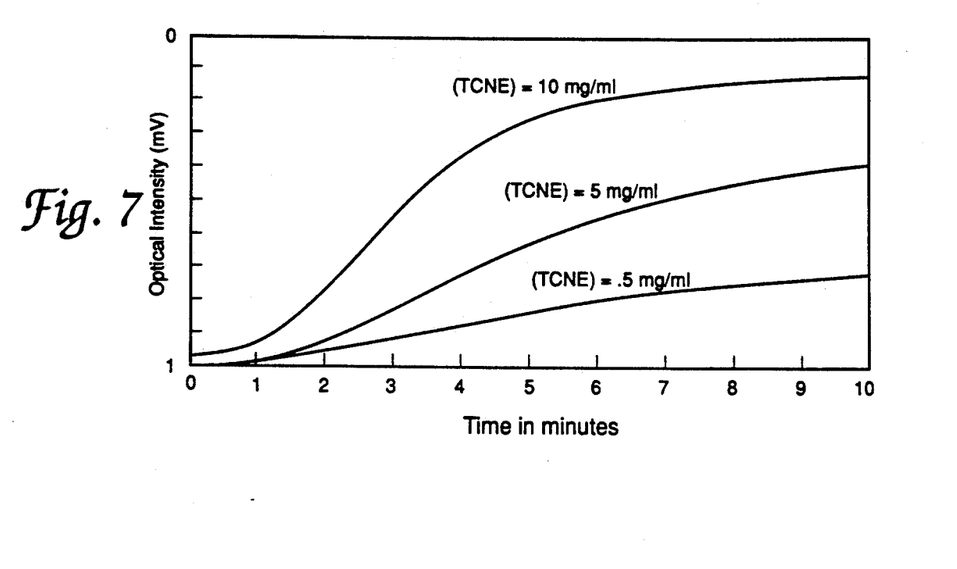
FIG. 7 is a plot of response to curves for a porous glass xylene sensor as a function of indicator concentration where the xylene concentration is 430 ppb.
Figure 8:
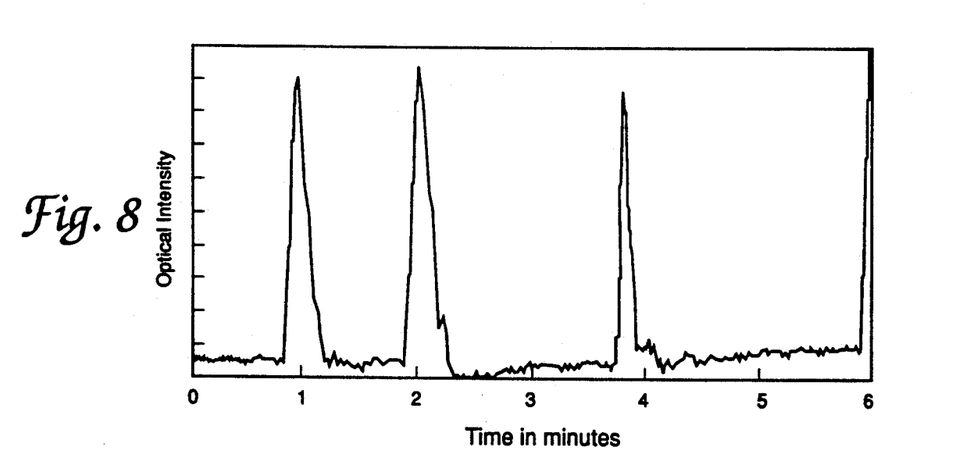
FIG. 8 is a time scan at 470 nm showing sensor response to repeated exposure to dichloromethane and indicating that there is no TCNE: solvent complex formed.

Experiments were performed with three different TCNE concentrations: 10 mg/ml, 5 mg/ml and 0.5 mg/ml. As shown in FIG. 7 the sensitivity increases at higher indicator concentrations; that is, for any given time interval the change in optical intensity is greater at higher indicator concentrations. The TCNE is dissolved in dichloromethane (DCM), and the response of a TCNE treated fiber (i.e., the sensor) to additional application of DCM is shown in FIG. 8. The DCM readily drys at room temperature with no change in original sensor transmission (i.e., no reaction of the TCNE with DCM).

Figure 9:
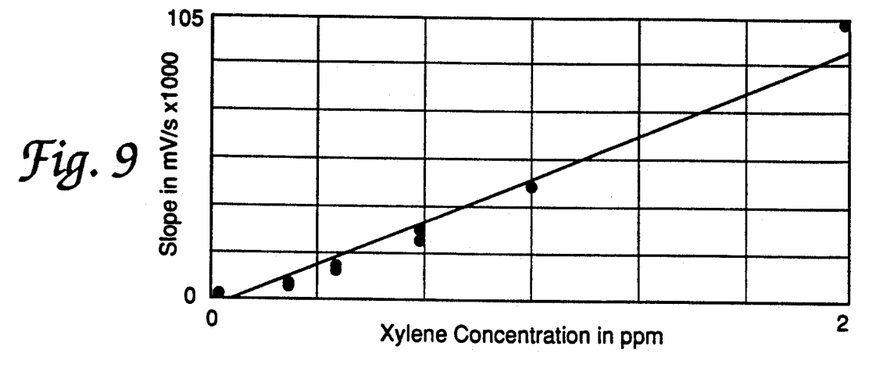
FIG. 9 is a calibration curve for a xylene optrode based on porous glass fiber; [TCNE]=5 mg/ml.
Figure 10:
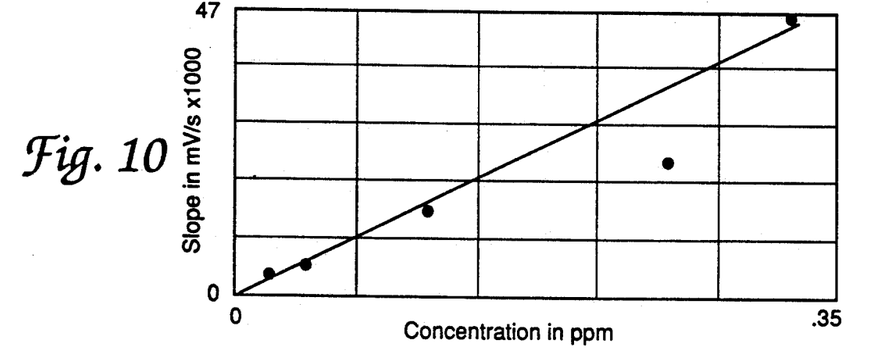
FIG. 10 is a calibration curve for a xylene optrode based on porous glass fiber; [TCNE]=0.5 mg/ml.
Figure 11:
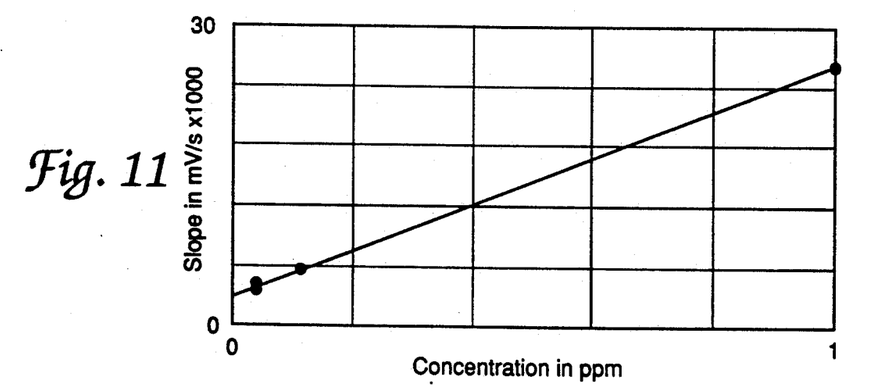
FIG. 11 is a calibration curve for a xylene optrode based on porous glass fiber; [TCNE]=10 mg/ml.

The TCNE reacts irreversibly with xylene to form a transient adduct under our experimental conditions. This implies that the reaction proceeds to saturation (i.e., when all the TCNE is consumed), rather than reaching some point of chemical equilibrium. Details of the kinetics are presented in Appendix B, and indicate that the slope of the intensity versus time plots are proportional to concentration. The plots of slope versus concentration are shown in FIGS. 9–11, and demonstrate good sensor linearity from the low parts per billion to low parts per million.

The slopes calculated from the intensity versus time curves show a reproducibility of ~5 percent, and are representative of a minimum of two experimental runs, and often more.

Figure 12:
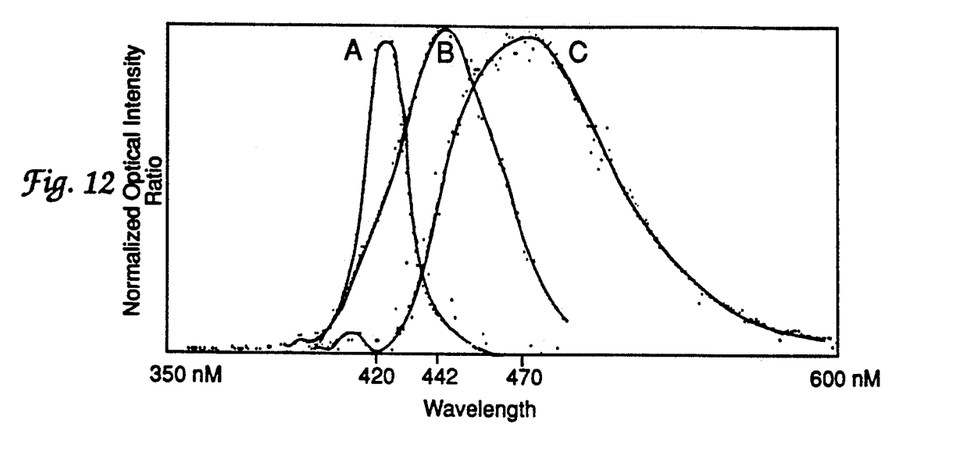
FIG. 12 is plot of aromatic hydrocarbon optrode response curves to benzene, toluene, and xylene, respectively.

Concept feasibility was demonstrated using o-xylene as the target aromatic hydrocarbon. Groundwater monitoring requires the measurement of the aromatic content known as BTEX (benzene, toluene, ethylbenzene and o-xylene). The quantification of benzene is of particular interest due to its carcinogenicity. Absorption curves for the optrode response to benzene, toluene and xylene are shown in FIG. 12. The absorption peaks for the TCNE:Ar-HC adduct are separated by approximately 30 nm suggesting that individual aromatic components may be quantified. The use of multi-wavelength techniques will be addressed in Phase II.

Non-aromatic hydrocarbons comprise approximately 80 percent of jet fuels. The indicator system was bench tested for responsivity to the saturated alkanes, octane, heptane, and a cyclic alkane.

Figure 13:
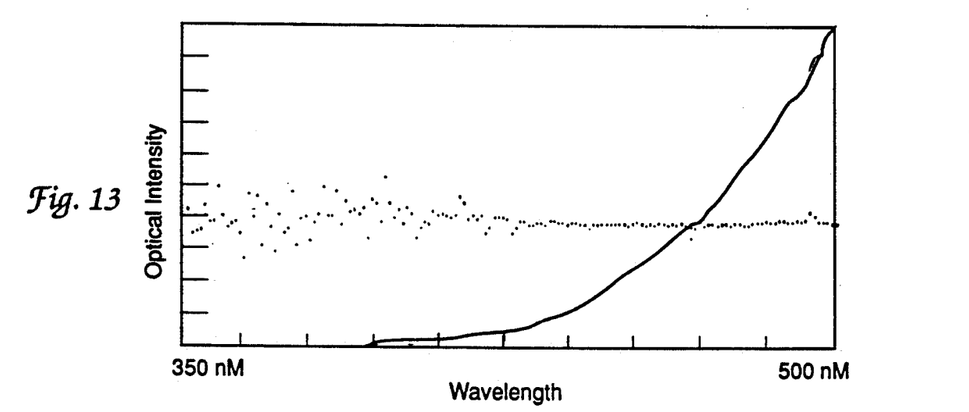
FIG. 13 is a plot of transmission as a function of wavelength for a porous glass sensor before and after exposure to octane.
Figure 14:
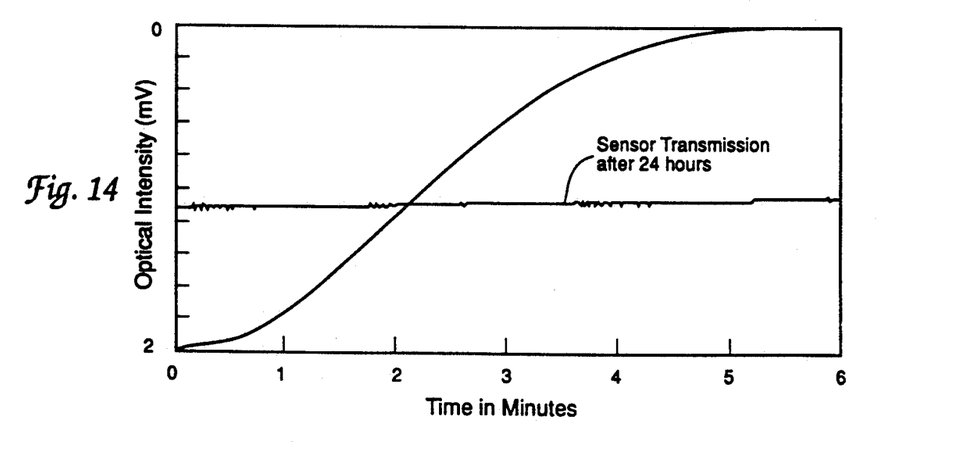
FIG. 14 is a plot of a response curve of a sensor to 0.4 ppm xylene and sensor recovery.

As shown in FIG. 13 the sensor is inert to these interferents. The ratio of sensor transmission before and after exposure to octane shows no change in the 350–500 nm region, and therefore, no response.

APPENDIX A

CALCULATIONS FOR ANALYTE CONCENTRATIONS ($C_{FEED}$)

The partial pressure of xylene at room temperature (25° C.):

6.55 torr

Using the ideal gas law to convert torr to moles/l we get:

6.55 torr = $3.54 \times 10^{-4}$ moles/l

Using an exemplary sparge flow rate we get a sparge concentration ($C_{SPARGE}$) of:

$C_{SPARGE}$ = moles/l *0.0053 l/min

OR $C_{SPARGE}$ = $1.87 \times 10^{-6}$ moles/min

Using the total flow rate we get a feed concentration ($C_{FEED}$) of:

$C_{FEED}$ = moles/min ÷ 0.6 l/min

OR $C_{FEED}$ = $3.11 \times 10^{-6}$ moles/l

Multiplying by the molecular weight of xylene:

$C_{FEED}$ = moles/l * 106.17 g/mole
     = $3.3 \times 10^{-4}$ g/l

Convert to ppb by dividing by the density:

$C_{FEED}$ = g/l ÷ 0.8802 g/ml ÷ 1000 ml/l $C_{FEED} \approx$ 375 ppb.

APPENDIX B

KINETIC MODEL FOR TCNE:XYLENE REACTION

Assuming the reaction is nonreversible and diffusion is the kinetic controlling step:

$$R = A D C_{xy} \qquad (1)$$

where R is the reaction rate of TCNE ($dC_{add}/dt$), A is a constant related to fiber properties, D is the xylene diffusion coefficient in the porous fiber, and $C_{xy}$ is the concentration of xylene outside the fiber.

The light intensity is a function of the concentration of the TCNE:xylene adduct ($C_{add}$):

$$I = I_0 \text{Exp}(-h\, C_{add}) \qquad (2)$$

where $I_0$ is the intensity of the incident light, h is the extinction coefficient (light absorption and light scattering by the adduct).

Initially the adduct concentration is very small and equation 2 can, therefore, be written as:

$$I = I_0(1 - h\, C_{add}) \qquad (3)$$

Taking the derivative of Equation 3, and substituting Equation 1 into the result $$\frac{dI}{dt} = -I_0 h\, A D C_{xy} \qquad (4)$$

Equation 4 suggests that the light intensity should show a linear decrease with time upon exposure to xylene, and that the slope of the decay curves (dI/dt) should be linearly proportional to the xylene concentration.

Having thus described the invention so that others skilled in the art may be able to understand and practice the same, it is expressly understood that various changes within the skill of the art may be made in the inventive optrode and in the method of fabricating same without departing from the spirit and scope of the invention, and that all such changes are deemed to be within the scope of the invention as defined by the appended claims.

What is claimed is:

1. In an optrode for in situ monitoring of chemical species wherein said optrode comprises a borosilicate optical fiber provided with a porous segment cast with a sensing reagent, the improvement wherein said chemical species comprise aromatic hydrocarbons and said sensing reagent is characterized by a sensitivity to less than 50 ppb, a response time less than 1 minute, excellent reproducibility and linearity, and specificity for said aromatic hydrocarbons.

2. The improved optrode of claim 1 wherein said aromatic hydrocarbons are those comprising the simple components of fuel.

3. The improved optrode of claim 2 wherein said aromatic hydrocarbons are selected from the group consisting of benzene, toluene, ethylbenzene and xylene.

4. the improved optrode of claim 3 wherein said reagent is TCNE.

5. The improved optrode of claim 1 wherein said sensing reagent is selected from the group consisting of TCNQ, fluorescein, $AgNO_3$, maleic anhydride, $I_2$ and TCNE.

6. The improved optrode of claim 1 wherein said reagent is capable of forming a $\pi$-type complex with said aromatic hydrocarbons.

* * * * *